United States Patent [19]

Mulder

[11] Patent Number: 4,721,798

[45] Date of Patent: Jan. 26, 1988

[54] PROCESS FOR EPOXIDATION OF OLEFINICALLY-UNSATURATED COMPOUNDS

[75] Inventor: Albertus J. Mulder, Amsterdam, Netherlands

[73] Assignee: Shell Oil Company, Houston, Tex.

[21] Appl. No.: 830,484

[22] Filed: Feb. 18, 1986

Related U.S. Application Data

[63] Continuation of Ser. No. 615,410, May 30, 1984, abandoned.

[30] Foreign Application Priority Data

Jun. 1, 1983 [GB] United Kingdom ............... 8315060

[51] Int. Cl.$^4$ ............................................. C07D 301/06
[52] U.S. Cl. ..................... 549/533; 549/332; 549/543; 549/544; 549/545; 549/546; 546/268
[58] Field of Search ............... 549/533, 332; 546/268

[56] References Cited

U.S. PATENT DOCUMENTS

| | | | |
|---|---|---|---|
| 3,346,473 | 10/1967 | Coffey et al. | 549/533 |
| 3,347,763 | 10/1967 | Coffey et al. | 549/533 |
| 3,379,737 | 4/1968 | Rustin et al. | 549/533 |
| 3,505,359 | 4/1970 | Rai et al. | 549/533 |
| 3,957,690 | 5/1976 | Bobolev et al. | 549/533 |
| 4,072,708 | 2/1978 | White et al. | 562/534 |
| 4,085,065 | 4/1978 | White et al. | 562/534 |
| 4,380,663 | 4/1983 | Roscher et al. | 562/536 |

FOREIGN PATENT DOCUMENTS

| | | | |
|---|---|---|---|
| 1161881 | 1/1964 | Fed. Rep. of Germany | 549/533 |
| 1293142 | 4/1969 | Fed. Rep. of Germany | 549/533 |

OTHER PUBLICATIONS

D. Rothe et al., Journal f. prakt. Chemie, vol. 324(4), (1982), pp. 596–608.

R. A. Sheldon et al., Metal-Catalyzed Oxidations of Organic Compounds, Academic Press, (1981), pp. 25–28.

Cherches, Kh. A., CA 87:183929y.

*Primary Examiner*—Norma S. Milestone

[57] ABSTRACT

The invention provides a process for epoxidizing an olefinic double bond in an olefinically-unsaturated compound by contact of a liquid phase mixture containing the olefinically-unsaturated compound, an aldehyde having at least two carbon atoms and a suitable solvent with molecular oxygen in the presence of a catalyst which is soluble in the reaction mixture and which comprises a praseodymium compound. The process has particularly advantageous application to oxidation of aldrin to dieldrin.

27 Claims, No Drawings

PROCESS FOR EPOXIDATION OF OLEFINICALLY-UNSATURATED COMPOUNDS

This is a continuation of application Ser. No. 615,410 filed May 30, 1984, now abandoned.

BACKGROUND OF THE INVENTION

This invention relates to a process for oxidation of olefinically-unsaturated compounds, and more specifically to a process for epoxidizing an olefinic compound in the presence of a soluble praseodymium catalyst.

The invention is useful in the synthesis of a broad range of epoxide compounds and specifically, for instance, in the conversion of allyl chloride to epichlorohydrin, and the preparation of dieldrin insecticide, and the preparation of a variety of aroma chemicals.

Numerous expidation processes are known in the prior art. Of particular interest is U.K. Patent Specification No. 963,430 which discloses a process for the epoxidation of an olefinic compound in which the double bond is in the terminal position and which contains at least 3 carbon atoms, by treatment of a liquid-phase mixture containing the olefinic compound and an aldehyde having at least two carbon atoms with oxygen, if desired in the presence of a solvent such as ethyl acetate and a catalyst which is preferably soluble in the reaction mixture, such as an organic cobalt or manganese salt.

Also of interest is U.S. Pat. No. 3,957,690 which discloses a process for the oxidation of propylene to propylene oxide, in the liquid phase, using a heterogeneous catalyst. The catalyst comprises a carrier with one or more oxides of scandium, yttrium, indium, gallium, thallium or rare-earth elements of the lanthanum group applied to its surface. Oxidation is effected using air, at high pressure, e.g., 50 atmospheres, and elevated temperature, e.g., 145° to 170° C. Conversion of propylene tends to be low, e.g., ranging from 13 to 32.5%.

SUMMARY OF THE INVENTION

The present invention provides a process for epoxidizing an olefinic double bond in an olefinically-unsaturated compound, which comprises contacting a liquid phase mixture of the olefinically-unsaturated compound, an aldehyde having at least two carbon atoms, and a suitable solvent with molecular oxygen in the presence of a catalyst which is soluble in the reaction mixture and which comprises a praseodymium compound.

DETAILED DESCRIPTION OF THE INVENTION

The process of this invention has been found to be suitable for general application to the epoxidation of a wide variety of unsaturated compounds. The process may, for example, be applied to $C_3$-$C_{30}$ olefins having from 1 to about 6 olefinic double bonds. The starting material optionally contains in the molecule one or more substituents such as ketonic carboxyl groups, one or more (e.g., particularly 1 to 3) alicyclic rings of 3 to 12 ring atoms each including fused rings, and/or one or more (e.g., particularly from one to about 5) substituent groups selected from —OH, —COOH, —CHO, —OR, —COOR, and —OCOR, in any of which R represents an alkyl or aryl group, for instance a $C_1$ to $C_6$ alkyl group (e.g., methyl or ethyl) or a phenyl or tolyl group. Other examples of optional substituents in the starting material include halo atoms (particularly chloro) and aryl substituents (e.g., phenyl, tolyl or pyridyl).

The invention is suitably applied to the epoxidation of compounds having more than one olefinic double bond, in which case the product is typically the mono-epoxide. Thus the process has particular utility in situations where selective epoxidation is desired.

In one particularly preferred embodiment, the invention is applied to epoxidize the pesticide aldrin to the pesticide dieldrin.

Although the invention is generally suitable for broad application, it has been found necessary to limit the description of suitable olefinically-unsaturated starting material in two particular instances. Attempts to practice the invention for the epoxidation of $\alpha,\beta$-unsaturated carboxylic acids, e.g., 2-pentenoic acid, crotonic acid or methacrylic acid, have failed to yield isolatable epoxide products. Similarly, it has not been practiced with reasonable success for the epoxidation of compounds containing a six membered ring wherein 3 to 4 member atoms are carbon atoms having $sp^2$ hybrid orbitals, e.g., isophorone, terpinolene, and $\ominus$-terpinene. Accordingly, it is to be understood that in describing the applicability of the invention to olefinically-unsaturated molecules, it is intended to exclude inoperable embodiments involving such $\alpha,\beta$-unsaturated carboxylic acids and such compounds having six-membered rings wherein 3 to 4 member atoms have $sp^2$ hybrid orbitals.

The aldehyde used in the process of the invention is suitably an aliphatic aldehyde, e.g., an aliphatic aldehyde containing 2 to 6 carbon atoms, or an aromatic aldehyde, e.g., benzaldehyde. Aliphatic aldehydes containing 2 to 4 carbon atoms are preferred. Propionaldehyde has been found to be very suitable. During the course of the reaction, the aldehyde is co-oxidized to the corresponding acid, e.g., propionaldehyde is oxidized to propionic acid.

The solvent may be any suitable solvent which is substantially inert to oxidation under the reaction conditions employed and which gives rise to a homogeneous reaction mixture. The solvent may be a single solvent or a mixture of solvents, and may, for example, conveniently be an ester, a ketone or a carboxylic acid. Advantageously the solvent comprises at least one solvent selected from $C_{1-6}$ alkyl esters of $C_{2-6}$ carboxylic acids, $C_{3-6}$ ketones and $C_{2-6}$ carboxylic acids, and more preferably the solvent comprises at least one solvent selected from methyl and ethyl esters of acetic and propionic acids, acetone, methyl ethyl ketone, acetic acid and propionic acid.

The catalyst is preferably in the form of one or more organic salts. More preferably, the catalyst comprises a $C_{2-6}$ carboxylic acid salt, particularly, the acetate or propionate salt, of praseodymium. The catalyst may if desired consist of a praseodymium salt alone or it may for example comprise a mixture of praseodymium and other metal salts, e.g., in the relative proportions in which they are found in nature. Conveniently therefore, the catalyst may comprise a didymium salt. It may sometimes by advantageous for the catalyst additionally to contain a cobalt salt, and/or a uranium or vanadium salt.

Relative quantities of olefinically-unsaturated starting material, aldehyde, solvent, and catalyst are not critical to the practice of the invention. The aldehyde is preferably used in an amount of at least about 1 mol per mol of olefinically-unsaturated compound. Preferably the amount of aldehyde is in the range from about 1 to 3 mol per mol of olefinically-unsaturated compound. Amounts of aldehyde in the range from about 1.1 to 2 mols per mol olefinically-unsaturated compound have been found to give very good results. The catalyst is employed in an effective amount, typically in an amount between about 0.001 and 5 percent by weight (%w) calculated on olefin starting material. Catalyst quantities between about 0.005 and 2%wt are preferred, while quantities between about 0.01 and 1.0%wt are considered most preferred. The quantity of solvent applied is that necessary to solubilize the olefine, aldehyde and catalyst components of the liquid mixture. Oxygen reactant is mixed with (for instance, bubbled through) the liquid mixture in a flow which will maintain the desired rate of reaction. Pure oxygen or mixtures of oxygen with other gases inert to the reaction mixture (e.g., air) are both suitable for purposes of the invention.

The process of the invention may be effected over a wide range of temperatures. Temperatures in the range from 30° C. to the reflux temperature of the reaction mixture are very suitable. Preferred reaction temperatures are in the range 30° to 60° C.

The invention will be further understood from the following examples thereof which were effected by the following general procedure, and wherein unless otherwise indicated parts, ratios and percentages are by weight and temperatures are in °C.

For each of the examples, a solution of the olefinically-unsaturated compound in the chosen solvent was heated under nitrogen to 48° C. in a reactor equipped with a mantle through which "FREON TF" (trade mark) (1,1,2-trichloro-1,2,2,-trifluoroethane, b.p. 48° C.) (also sold as "FREON 113") (trade mark) was circulated as heat-exchange medium, by means of which reaction temperatures were generally maintained in the range 48° to 53° C., unless otherwise stated. Catalyst was introduced as a solution in a suitable solvent (which in appropriate cases was the said chosen solvent, but in other cases was acetic or propionic acid).

Propionaldehyde was streamed at constant rate into the reaction mixture and the nitrogen was replaced by oxygen or air. The propionaldehyde was added over the course of 1 to 3 hours, depending on the rate of reaction. The course of the reaction was monitored by hourly withdrawal of a sample which was analyzed by gas chromatoography, or in some cases by nuclear magnetic resonance or infra-red spectroscopy. Loss of propionaldehyde from the reactor was minimized by means of condensers at 10° C. and −20° C. coupled in series, condensate being returned to the reactor.

Reaction was terminated by replacing the oxygen or air by nitrogen and cooling the reactor to ambient temperature (20° C.). After filtration, the reaction mixture, the solvent and the propionic acid produced during the course of the reaction were, in suitable cases (in which the boiling temperatures of the desired end products is significantly lower than those of the solvent and propionic acid, as will be well understood by those skilled in the art), removed under vacuum at temperatures below 60° C. In other cases the reaction mixture was diluted with pentane, washed with saturated aqueous sodium chloride to remove water-soluble species (mostly propionic acid), and volatiles were removed by vacuum distillation. products were identified by nuclear magnetic resonance and infrared spectroscopy and using gas-liquid chromatography.

In the examples which follow, "Di(acetate)$_3$" was didymium acetate (obtained from Lindsay Chemicals Division) from which water had been removed by drying in vacuo at 100° C. before grinding to a fine powder, having the following metal oxide composition: (in percent by weight) La$_2$O$_3$ (41.83%), CeO$_2$ (0.11%), Pr$_6$O$_{11}$ (17.37%), Nd$_2$O$_3$ (29.71%), Sm$_2$O$_3$ (5.03%), Gd$_2$O$_3$ (3.20%), Yb$_2$O$_3$ (0.46%) and remainder (Eu$_2$O$_3$, Pm$_2$O$_3$, Tb$_2$O$_3$, Dy$_2$O$_3$, Ho$_2$O$_3$, Er$_2$O$_3$, Tm$_2$O$_3$, Lu$_2$O$_3$) (2.29%).

Other didymium salts and mixtures were prepared in known manner from this didymium acetate.

EXAMPLES 1 TO 8

Epoxidation of dodecene-1

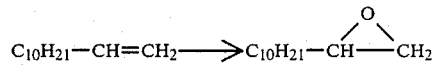

Dodecene-1 was epoxidized by the above procedure using a variety of catalysts and using solvent appropriate to the catalyst employed. In each case 0.5 mol dodecene-1 was employed, the volume ratio solvent to dodecene-1 was 3:1, propionaldehyde was added at a rate of 15 ml/h to a final mol. ratio of propionaldehyde to dodecene-1 of 1.6:1, and oxygen was bubbled through the reaction mixture at a rate from 6 to 10 l/hour.

Details of the catalyst used and their quantities, nature of solvent, reaction times, overall molar conversions of dodecene-1 and selectivities to the desired epoxide and product are given in Table I following:

TABLE I

| Example | Catalyst (ratios are by weight) | Catalyst quantity, % wt. based on olefin | Solvent | Reaction time, hr. | Conversion of olefins, % mol | Selectivity to epoxide, % |
|---|---|---|---|---|---|---|
| 1 | Pr(acetate)$_3$ | 0.01 | ethyl acetate | 6 | 91 | 87 |
| 2 | Di(acetate)$_3$ | 1.0 | ethyl acetate | 7 | >96 | 82 |
| 3 | Di(acetate)$_3$/ Co(acetate)$_2$ (100:1) | 0.5 | ethyl acetate | 5 | >96 | 88 |
| 4 | Di(propionate)$_3$ (20% solution in propionic acid) | 0.5 | ethyl acetate | 6 | 91 | 89 |
| 5 | Di(propionate)$_3$/ Co(propionate)$_3$ (100:1)(20% solution | 0.6 | ethyl acetate | 3 | >96 | 88 |

TABLE I-continued

| Example | Catalyst (ratios are by weight) | Catalyst quantity, % wt. based on olefin | Solvent | Reaction time, hr. | Conversion of olefins, % mol | Selectivity to epoxide, % |
|---|---|---|---|---|---|---|
| 6 | Di(propionate)$_3$/VO(propionate)/Co(propionate)$_2$ (1:0.78:7 × 10$^{-4}$)$^2$ (20% solution in propionic acid) | 0.5 | ethyl acetate | 3 | 93 | 91 |
| 7 | Di(propionate)$_3$/UO$_2$(propionate)$_2$ (1:0.27)(10% solution in propionic acid) | 0.8 | ethyl acetate | 5 | >96 | 86 |
| 8 | Di(propionate)$_3$/UO$_2$(propionate)$_2$/Co(propionate)$_2$ (1:0.27:10$^{-5}$) (10% solution in propionic acid) | 0.8 | ethyl acetate | 3 | >96 | 94 |
| Comparative A | Co(acetate)$_2$ | 1.0 | acetic acid | 8 | 48 | 32 |
| Comparative B | Mn(acetate)$_3$ | 0.8 | ethyl acetate | 6 | 92 | 70 |
| Comparative C | Mn(acetate)$_3$/Co(acetate)$_2$ (100:1) | 0.8 | acetic acid | 5 | 68 | 68 |
| Comparative D | Mn(acetate)$_3$/Co(acetate)$_2$ (100:1) | 0.8 | acetone | 8 | 76 | 62 |
| Comparative E | La(acetate)$_3$ | 0.01 | ethyl acetate | 6 | 12 | 50 |
| Comparative F | Ce(acetate)$_3$ | 0.01 | ethyl acetate | 6 | 65 | 10 |
| Comparative G | Nd(acetate)$_3$ | 0.01 | ethyl acetate | 6 | 5 | trace |
| Comparative H | Eu(acetate)$_3$ | 0.01 | ethyl acetate | 6 | 23 | 72 |
| Comparative I | Gd(acetate)$_3$ | 0.01 | ethyl acetate | 6 | 5 | trace |
| Comparative J | Tb(acetate)$_3$ | 0.01 | ethyl acetate | 6 | 52 | 68 |
| Comparative K | Yb(acetate)$_3$ | 0.01 | ethyl acetate | 6 | 11 | 69 |
| Comparative L | Heterogeneous catalyst$^a$ | 5 | ethyl acetate | 12 | 12 | 56 |

$^a$Di(acetate)$_3$/Co(acetate)$_2$ (100:1), 10% solution in acetic acid, was used to impregnate silica balls of average diameter 0.5 mm, surface area 275 m$^2$/g and pore volume 1.1 ml/g, and the balls were subsequently heated for 24h at 400° C. Catalyst was added as a suspension in ethyl acetate.

EXAMPLE 9

Conversion of Aldrin to Dieldrin

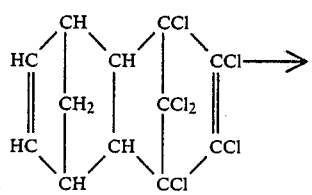

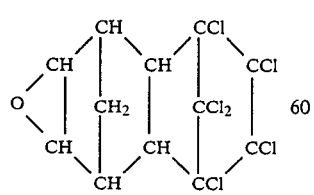

Aldrin was epoxidized to Dieldrin by the above procedure using as catalyst a mixture of Di(acetate)$_3$ and Co(acetate)$_2$ (weight ratio 100:1) and ethyl acetate as solvent. The volume ratio solvent to Aldrin was 3:1, the final mol ratio of propionaldehyde to Aldrin was 1.7:1, air was bubbled through the reaction mixture at a rate of 100 liters/hour (per 100 ml reaction mixture), the catalyst was used at a level of 1.6%wt based on the weight of aldrin, and reaction was continued for 15 hours.

The ethyl acetate and propionic acid were evaporated off, leaving a solid white residue which was dissolved in dichloromethane, washed with aqueous sodium bicarbonate solution and evaporated to give a white solid product (100% yield based on starting material) which contained 95%wt Dieldrin (as determined by gas-liquid chromatography and nuclear magnetic resonance), the remainder being mainly unconverted Aldrin.

EXAMPLE 10

Epoxidation of camphene

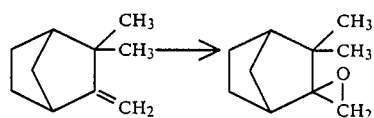

Camphene was epoxidized by the above-described procedure using the same catalyst as in Example 9 (0.8% based on the weight of camphene, and ethyl acetate as solvent (volume ratio solvent to camphene 3:1). The final mol ratio propionaldehyde to camphene was 1.6:1, oxygen was bubbled through at a rate of 10 liters/hour, and reaction time was 5 hours.

86% conversion of starting material was obtained with selectivity to desired epoxide product of 92%.

By comparison when Mn(acetate)$_3$ was used as catalyst in a comparable procedure, with acetic acid as solvent, after 7 hours reaction time 94% of camphene was consumed with selectivity to desired epoxide product less than 5%.

EXAMPLE 11

Epoxation on longifilene

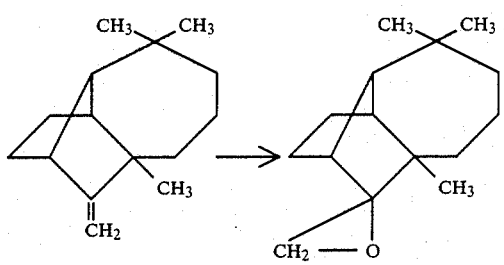

Longifilene was epoxidized by the above procedure and under the same conditions as in Example 10 except that 1% of catalyst based on the weight of longifilene was employed and reaction time was 5.5 hours. Greater than 96% conversion of longifilene took place, with 81% selectivity to the desired epoxide.

By comparison, when Mn(acetate)$_3$/Co(acetate)$_2$ (100:1 by weight) was used as catalyst in a comparable procedure with acetic acid as solvent, after 3 hours more than 96% of the longifilene had been consumed but no epoxide was detectable (product contained 61% ketone and 32% acid).

EXAMPLE 12

Epoxidation of -3-carene

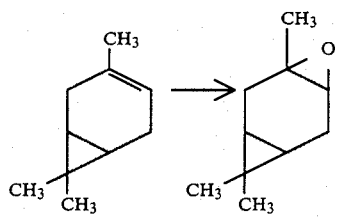

Δ-3-carene was epoxidized by the above-described procedure, using Di(acetate)$_3$ as catalyst (1% based on the weight of Δ-3-carene) and ethyl acetate as solvent (volume ratio solvent to Δ-3-carene 3:1). The final mol ratio propionaldehyde to Δ-3-carene was 1.5:1, oxygen was bubbled through at a rate of 8 liters/hour, and reaction time was 4 hours.

95% conversion of starting material was obtained with selectivity to desired epoxide product of 82%.

By comparison, when Mn(acetate)$_3$ was used as catalyst in a comparable procedure, with acetic acid as solvent, after 8 hours reaction time 28% of Δ-3-carene was consumed with selectivity to desired epoxide being less than 5%, much of the product being a polymeric black tar.

EXAMPLE 13

Epoxidation of α-pinene

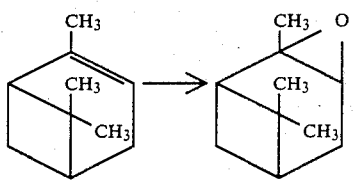

α-pinene was epoxidized by the above procedure, using Di(acetate)$_3$ as catalyst (1% based on the weight of starting material) and ethyl acetate as solvent (volume ratio solvent to starting material 2:1). The final mol ratio propionaldehyde to starting material was 1.4:1, oxygen was bubbled through at a rate of 6 liters/hour, and reaction time was 8 hours.

92% conversion of starting material was obtained, with selectivity to desired epoxide product of 73%.

By comparison, when Mn(acetate)$_3$ was used as catalyst in a comparable procedure, with acetic or propionic acid as solvent, after 6 hours reaction time more than 96% of starting material was consumed, with selectivity to desired epoxide of less than 5%, the product being mostly in the form of a thick black tar.

EXAMPLE 14

Epoxidation of β-pinene

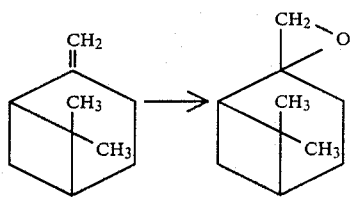

β-pinene was epoxidized by the above procedure, using Di(acetate)$_3$ as catalyst (1% based on the weight of starting material and ethyl acetate as solvent (volume ratio solvent to starting material 2:1). The final mol ratio propionaldehyde to starting material was 1.4:1, oxygen was bubbled through at a rate of 6 liters/hour, and reaction time was 5 hours.

83% conversion of starting material was obtained, with selectivity to desired epoxide product of 48%.

By comparison, when Mn(acetate)$_3$ was used as catalyst in a comparable procedure, with propionic acid as solvent, after 9 hours reaction time more than 96% of starting material was consumed, with selectivity to desired epoxide of less than 5%, the product being in the form of a black tar.

EXAMPLE 15

Epoxidation of 2,4,4-trimethylpentene

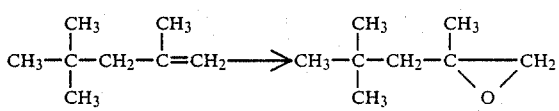

2,4,4-trimethylpentene was epoxidized by the above procedure, using Di(acetate)₃ as catalyst (0.8% based on the weight of starting material) and ethyl acetate as solvent (volume ratio solvent to starting material 2.5:1). The final mol ratio propionaldehyde to starting material was 1.1:1, oxygen was bubbled through at a rate of 6 liters/hour, and reaction time was 6 hours.

More than 96% conversion of starting material was obtained, with selectivity to desired epoxide product of 89%. Some propionate esters of diols were produced, but no ketone.

By comparison, when Mn(acetate)₃ was used as catalyst in a comparable procedure, with acetic acid as solvent, after 18 hours reaction time more than 96% of starting material was consumed, with selectivity to desired epoxide of 74%. At least 20% of the reaction product was in the form of ketone.

EXAMPLE 16

Epoxidation of pentene-1

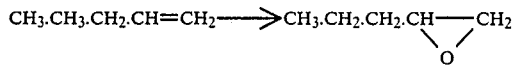

Pentene-1 was epoxidized by the above procedure, using a Di(acetate)₃/Co(acetate)₂ catalyst (100:1 by weight) and also with Di(acetate)₃ as catalyst (1% based on the weight of starting material in each case) and ethyl acetate as solvent (volume ratio solvent to starting material 3:1). The final mol ratio propionaldehyde to starting material was 1.6:1, oxygen was bubbled through at a rate of 6 liter/hours in the first case and 9 liter/hour in the second case, reaction time was 6 hours in the first case and 5.5 hours in the second case and reaction temperature was 31° C. in the first case and 35° C. in the second case.

In the first case more than 96% conversion of starting material was obtained, with selectivity to desired epoxide product of 86%.

In the second case 92% of starting material was consumed, with selectivity to desired epoxide of 78%.

EXAMPLE 17

Epoxidation of 2,6-dimethylheptadiene

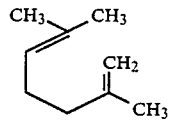

2,6-dimethylheptadiene was epoxidized by the above procedure, using Di(acetate)₃/Co(acetate)₂ (100:1 by weight) as catalyst (0.5% based on the weight of starting material) and ethyl acetate as solvent (volume ratio solvent to starting material 1.5:1). The final mol ratio propionaldehyde to starting material was 1.2:1, oxygen was bubbled through at a rate of 7 liters/hour, and reaction time was 3.5 hours.

More than 96% conversion of starting material was obtained, with selectivity to the 2-epoxide product of 87%.

By comparison, when Mn(acetate)₃ was used as catalyst in a comparable procedure, with acetic acid/ethyl acetate as solvent, after 4 hours reaction time 92% of starting material was consumed, with selectivity to desired epoxide of 81%.

EXAMPLE 18

Epoxidation of dihydromyrcene

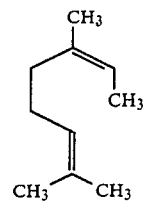

Dihydromyrcene was epoxidized by the above procedure, using Di(propionate)₃/Co(propionate)₂ (100:1 by weight) (20% solution in propionic acid) as catalyst (0.6% based on the weight of starting material) and ethyl acetated as solvent (volume ratio solvent to starting material 3:1). The final mol ratio propionaldehyde to starting material was 1.1:1, oxygen was bubbled through at a rate of 6 liters/hour, and reaction time was 3.5 hours.

More than 96% conversion of starting material was obtained, with selectivity to mono epoxide product of 82%. A small amount of diepoxide product was also obtained.

EXAMPLE 19

Epoxidation of geraniol

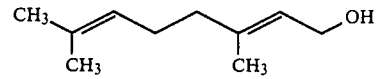

Geraniol was epoxidized by the above procedure, using the same catalyst as in Example 18 (0.8% based on the weight of starting material) and ethyl acetate as solvent (volume ratio solvent to starting material 2.5:1). The final mol ratio propionaldehyde to starting material was 1.5:1, oxygen was bubbled through at a rate of 8 liters/hour, and reaction times was 5 hours.

81% conversion of starting material was obtained, with selectivity to monoepoxide product of 78%, the mono epoxide product being a mixture of 2- and 6-epoxides.

EXAMPLE 20

Epoxidation of citral

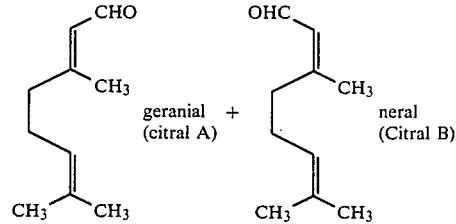

Citral, the naturally-occurring mixture of geranial and neral isolable from oil of lemon grass was epoxidized by the above procedure, using the same catalyst as in Examples 18 and 19 (1% based on the weight of starting material) and acetone as solvent (volume ratio solvent to starting material 2:1). The final mol ratio propionaldehyde to starting material was 2:1, oxygen was bubbled through at a rate of 6 liters/hour, and reaction time was 4.5 hours.

More than 96% conversion of starting material was obtained, with selectivity to 6-epoxide products of 68%.

EXAMPLE 21

Epoxidation of α-limonene

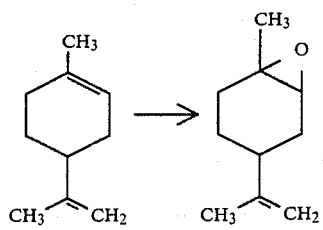

α-limonene was epoxidized by the above-described procedure, using Di(acetate)$_3$ as catalyst (1% based on the weight of starting material) and ethyl acetate as solvent (volume ratio solvent to starting material 3:1). The final mol ratio propionaldehyde to starting material was 1.5:1, oxygen was bubbled through a rate of 6 liters/hour, and reaction time was 4.5 hours.

94% conversion of starting material was obtained, with selectivity to mono epoxide products of 81% (cis:-trans, 2:1 [α]$_{20}$D −42°). Ten percent diepoxide was produced.

By comparison, when Mn(acetate)$_3$/Co(acetate)$_2$ (100:1 by weight) was used as catalyst in a comparable procedure, with acetic acid/ethyl acetate as solvent, after 10 hours reaction time 82% of starting material was consumed, with selectivity to mono epoxide of only 22%, the remainder being a mixture of ketones, diols and phenols.

EXAMPLE 22

Epoxidation of 1,11-dodecadiene

1,11-dodecadiene was epoxidized by the above-described procedure, using the same catalyst as in Examples 18 to 20 as catalyst (1% based on the weight of starting material) and ethyl acetate as solvent (volume ratio solvent to starting material 2:1). The final mol ratio propionaldehyde to starting material was 1.2:1, oxygen was bubbled through at a rate of 6 liters/hour, and reaction time was 3.5 hours.

More than 96% conversion of starting material was obtained, with selectivity to mono epoxide product of 91%. A small amount of diepoxide was also produced.

EXAMPLE 23

Epoxidation of 1,3-nonadiene

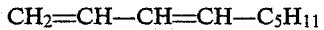

1,3-nonadiene was epoxidized by the above-described procedure, using the same catalyst as in Example 22 (0.5% based on the weight of starting material) and ethyl acetate as solvent (volume ratio solvent to starting material 3:1). The final mol ratio priopionaldehyde to starting material was 1.5:1, oxygen was bubbled through at a rate of 6 liters/hour, and reaction time was 5 hours.

71% conversion of starting material was obtained, with selectivity to mono epoxide product of 58%, the remainder being a polymeric material.

EXAMPLE 24

Epoxidation of squalene

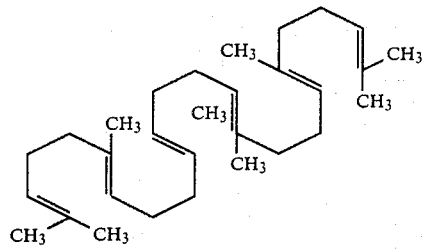

Squalene was epoxidized by the above-described procedure, using the same catalyst as in Examples 22 and 23 as catalyst (1% based on the weight of starting material) and ethyl acetate as solvent (volume ratio solvent to starting material 2:1). The final mol. ratio propionaldehyde to starting material was 1.2:1, oxygen was bubbled through at a rate of 8 liters/hour, and reaction time was 4 hours.

72% conversion of starting material was obtained, with selectivity to mono epoxide product of 36%. Infrared and nuclear magnetic resonance spectroscopy indicated that the remainder was a complex structure of steroid configuration.

By comparison, when Mn(acetate)$_3$ was used as catalyst in a comparable procedure, with acetic acid/ethyl acetate as solvent, after 3.5 hours reaction time more than 96% of starting material was consumed, but no epoxide was present in the product, which was a complex structure of steroid configuration.

EXAMPLE 25

Epoxidation of allyl acetate

Allyl acetate was epoxidized by the above-described procedure, using Di(acetate)$_3$ as catalyst (1% based on the weight of starting material) and ethyl acetate as solvent (volume ratio solvent to starting material 3:1). The procedure was similar to the general procedure described above except that ethyl acetate was heated in the reactor to 48° C., the catalyst was introduced and a blend of the allyl acetate propionaldehyde and more ethyl acetate was streamed into the reactor at constant rate while the oxygen was bubbled through the reaction mixture. The final mol ratio propionaldehyde to starting material was 2:1, oxygen was bubbled through at a rate of 10 liters/hour, and reaction time was 5 hours.

95% conversion of starting material was obtained, with selectivity to desired epoxide product of 63%, 12% being ethyl acetoacetate.

EXAMPLE 26

Epoxidation of allyl chloride

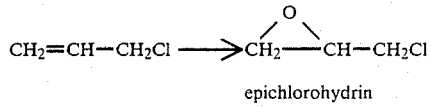

epichlorohydrin

Allyl chloride was epoxidized by a procedure similar to that of Example 26 using Di(acetate)₃ as catalyst (1% based on the weight of starting material) and ethyl acetate as solvent (volume ratio solvent to starting material 3:1). The final mol ratio propionaldehyde to starting material was 2:1, oxygen was bubbled through at a rate of 8 liters/hour, and reaction time was 7 hours.

63% conversion of starting material was obtained, with selectivity to desired epoxide product of 60%, the remainder being a polymeric mass.

EXAMPLE 27

Epoxidation of allyl alcohol

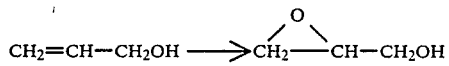

Allyl alcohol was epoxidized by the above-described general procedure, using Di(acetate)₃/Co(acetate)₂ (100:1 by weight) as catalyst (1% based on the weight of starting material), acetone as solvent (volume ratio solvent to starting material 3:1). The final mol ratio propionaldehyde to starting material was 2:1, oxygen was bubbled through at a rate of 10 liters/hour, and reaction time was 6 hours.

91% conversion of starting material was obtained, with selectivity to desired epoxide product of 43%, the remainder being a polymeric mass.

EXAMPLE 28

Epoxidation of allyl phenyl ether

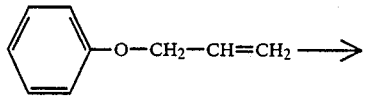

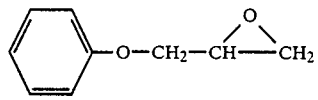

Allyl phenyl ether was epoxidized by the above-described procedure, using Di(acetate)₃/Co(acetate)₂ (100:1 by weight) as catalyst (1% based on the weight of starting material), acetone as solvent (volume ratio solvent to starting material 3:1). The final mol ratio propionaldehyde to starting material was 2:1, oxygen was bubbled through at a rate of 8 liters/hour, and reaction time was 7 hours.

38% conversion of starting material was obtained, with selectivity to desired epoxide product of 41%, 20% being phenol and the remainder a black tar.

EXAMPLE 29

Epoxidation of ally o-tolyl ether

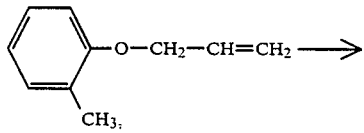

-continued

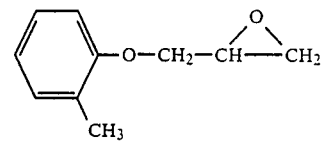

Ally o-tolyl ether was epoxidized by the above-described procedure, using Di(acetate)₃/Co(acetate)₂ (100:1 by weight) as catalyst (1% based on the weight of starting material), acetone as solvent (volume ratio solvent to starting material 3:1). The final mol ratio propionaldehyde to starting material was 2:1, oxygen was bubbled through at a rate of 8 liters/hour, and reaction time was 6 hours.

62% conversion of starting material was obtained, with selectivity to desired epoxide product of 22%, 15% being o-cresol and the remainder a black tar.

EXAMPLE 30

Epoxidation of 1,2,3,6-tetrahydrobenzoic acid

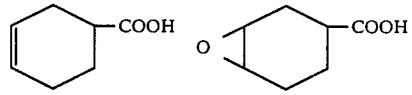

1,2,3,6-tetrahydrobenzoic acid was epoxidized by the above-described procedure, using Di(acetate)₃ as catalyst (0.5% based on the weight of starting material), ethyl acetate as solvent (volume ratio solvent to starting material 3:1). The final mol ratio propionaldehyde to starting material was 1.6:1, oxygen was bubbled through at a rate of 5 liters/hour, and reaction time was 5 hours.

More than 96% conversion of starting material was obtained, with selectivity to desired epoxide product of 82%.

EXAMPLE 31

Epoxidation of 4-pentenoic acid

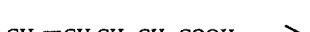

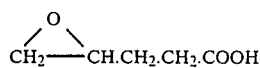

4-pentenoic acid was epoxidized by the above-described procedure, using Di(acetate)₃/Co(acetate)₂ (100:1 by weight) as catalyst (0.5% based on the weight of starting material), ethyl acetate as solvent (volume ratio solvent to starting material 3:1). The final mol ratio propionaldehyde to starting material was 1.8:1, oxygen was bubbled through at a rate of 6 liters/hour, and reaction time was 6 hours.

More than 96% conversion of starting material was obtained, with selectivity to desired epoxide product of 68%, the remainder being predominantly a complex mixture of esters.

By comparison, when, β-unsaturated acids, namely 2-pentenoic acid, crotonic acid and methacrylic acid, were subject to comparable procedures, in each case more than 96% of the starting material was consumed, but no epoxide product was obtained, the only products

EXAMPLES 32

Epoxidation of ethyl crotonate

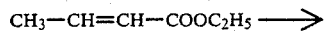

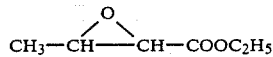

Ethyl crotonate was epoxidized by the above-described procedure, using Di(acetate)₃/Co(acetate)₂ (100:1 by weight) as catalyst (0.8% based on the weight of starting material) and acetone as solvent (volume ratio solvent to starting material 3:1). The final mol ratio propionaldehyde to starting material was 1.6:1, oxygen was bubbled through at a rate of 9 liters/hour, and reaction time was 6 hours.

43% conversion of starting material was obtained, with selectivity to desired epoxide product 68%, the remainder being a polymeric material.

EXAMPLE 33

Epoxidation of ethyl methacrylate

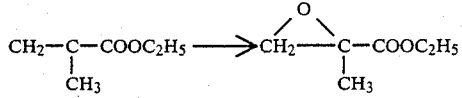

Ethyl methacrylate was epoxidized by the above-described procedure, using Di(acetate)₃/Co(acetate)₂ (100:1 by weight) as catalyst (0.8% based on the weight of starting material) and acetone as solvent (volume ratio solvent to starting material 3:1). The final mol ratio propionaldehyde to starting material was 1.6:1, oxygen was bubbled through at a rate of 9 liters/hour, and reaction time was 7 hours.

52% conversion of starting material was obtained, with selectivity to desired epoxide product of 73%.

EXAMPLE 34

Epoxidation of 2-allyl pyridine

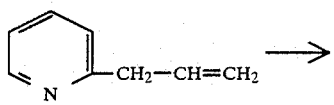

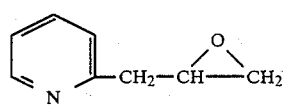

2-allyl pyridine was epoxidized by the above-described procedure, using Di(acetate)₃/Co(acetate)₂ (100:1 by weight) as catalyst (0.5% based on the weight of starting material) and ethyl acetate as solvent (volume ratio solvent to starting material 4:1). The final mol ratio propionaldehyde to starting material was 1.2:1, oxygen was bubbled through at a rate of 6 liters/hour, and reaction time was 6 hours.

More than 96% conversion of starting material was obtained, with selectivity to desired epoxide product of 23%, the remainder being a polymeric black tar which was insoluble in ethyl acetate.

EXAMPLE 35

Epoxidation of 3-allyl pyridine

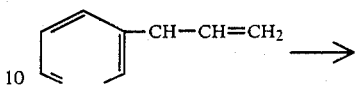

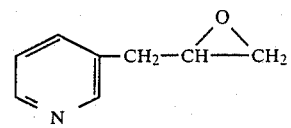

3-allyl pyridine was epoxidized by the same procedure as in Example 35.

More than 96% conversion of starting material was obtained, with selectivity to desired epoxide product of 71%, and very little polymer formation.

EXAMPLE 36

Epoxidation of 2,3-dimethyl-2-butene

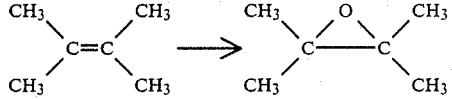

2,3-dimethyl-2-butene was epoxidized by the above-described procedure, using Di(acetate)₃/Co(acetate)₂ (100:1 by weight) as catalyst (1% based on the weight of starting material) and ethyl acetate as solvent (volume ratio solvent to starting material 3:1). The final mol ratio propionaldehyde to starting material was 1.8:1, oxygen was bubbled through at a rate of 6 liters/hour, reaction time was 3 hours and reaction temperature was 40° C.

67% conversion of starting material was obtained, with selectivity to desired epoxide product of 42%.

By comparison, when Mn(acetate)₃/Co(acetate)₂ (100:1 by weight) was used as catalyst in a comparable procedure, with acetic acid as solvent, after 6 hours reaction time 72% of starting material was consumed, but no epoxide was produced.

EXAMPLE 37

Epoxidation of α-methylstyrene

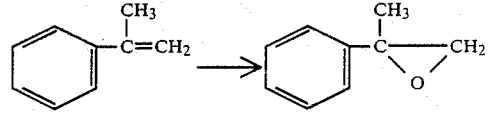

α-methylstyrene was epoxidized by the above-described procedure, using Di(acetate)₃/Co(acetate)₂ (100:1 by weight) as catalyst (1% based on the weight of starting material) and acetone as solvent (volume ratio of solvent to starting material 2:1). The final mol ratio propionaldehyde to starting material was 1.5:1, oxygen was bubbled through at a rate of 6 liters/hour, and reaction time was 3 hours.

93% conversion of starting material was obtained, with selectivity to desired epoxide product of 67%. About 21% of the starting material was converted to acetophenone.

By comparison, when Mn(acetate)₃/Co(acetate)₂ (100:1 by weight) was used as catalyst in a comparable procedure, with acetic acid as solvent, after 4 hours reaction time more than 96% of starting material was consumed, with selectivity to desired epoxide of less than 3%.

EXAMPLE 38

Epoxidation of cyclododecene

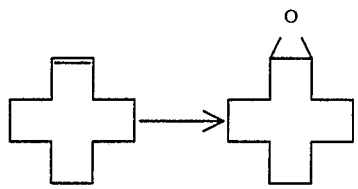

Cyclododecene was epoxidized by the above-described procedure, using Di(acetate)₃/Co(acetate)₂ (100:1 by weight) as catalyst (0.6% based on the weight of starting material) and ethyl acetate as solvent (volume ratio solvent to starting material 3:1). The final mol ratio propionaldehyde to starting material was 1.2:1, oxygen was bubbled through at a rate of 8 liters/hour, and reaction time was 3.5 hours.

More than 96% conversion of starting material was obtained, with selectivity to desired epoxide product of 81%.

By comparison, when Mn(acetate)₃ was used as catalyst in a comparable procedure, with acetic acid as solvent, after 4 hours reaction time 78% of starting material was consumed, with selectivity to desired epoxide of 76%.

EXAMPLE 39

Epoxidation of cyclododecatriene

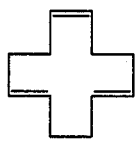

Cyclododecatriene was epoxidized by the above-described procedure, using Di(acetate)₃ as catalyst (1% based on the weight of stating material) and ethyl acetate as solvent (volume ratio solvent to starting material 2:1). The final mol ratio propionaldehyde to starting material was 1.5:1, oxygen was bubbled through at a rate of 8 liters/hour, and reaction time was 6 hours.

More than 96% conversion of starting material was obtained, with selectivity to mono epoxide product of 85%.

By comparison, when Mn(acetate)₃ and Mn(acetate)₃/Co(acetate)₂ (100:1 by weight) were used as catalysts in comparable procedures, with ethyl acetate/acetic acid and acetic acid, respectively as solvents, after 4 and 7 hours reaction time respectively, in the first case over 90% of starting material was consumed, with selectivity to mono epoxide of only 78%, and in the second case 88% of starting material was consumed, with selectivity to mono epoxide of 66%.

EXAMPLE 40

Epoxidation of 1,5,9-trimethylcyclododecatriene

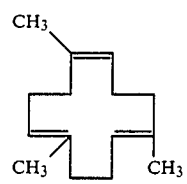

1,5,9-trimethylcyclododecatriene was epoxidized by the above-described procedure, using Di(acetate)₃/Co(acetate)₂ (100:1 by weight) as catalyst (0.7% based on the weight of starting material) and ethyl acetate as solvent (volume ratio solvent to starting material 3:1). The final mol ratio propionaldehyde to starting material was 2:1, oxygen was bubbled through at a rate of 10 liters/hour, and reaction time was 7 hours.

91% conversion of starting material was obtained, with selectivity to mono epoxide product of 88%, no diepoxide being detectable.

By comparison, when Mn(acetate)₃ was used as catalyst in a comparable procedure, with ethyl acetate/acetic acid as solvent, after 7.5 hours reaction time 83% of starting material was consumed with selectivity to desired epoxide of 81%. Small amounts of diepoxide were produced.

EXAMPLE 41

Epoxidation of cyclooctene

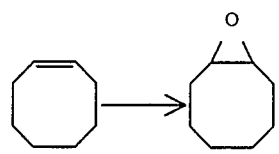

Cyclooctene was epoxidized by the above-described procedure, using Di(acetate)₃/Co(acetate)₂ (100:1 by weight) as catalyst (1% based on the weight of starting material) and ethyl acetate as solvent (volume ratio solvent to starting material 2.5:1). The final mol ratio propionaldehyde to starting material 1.6:1, oxygen was bubbled through at a rate of 10 liters/hour, and reaction time was 6 hours.

More than 96% conversion of starting material was obtained, with selectivity to desired epoxide product of 90%.

By comparison, when Mn(acetate)₃/Co(acetate)₂ (100:1 by weight) was used as catalyst in a comparable procedure, with ethyl acetate as solvent, after 9 hours reaction time 82% starting material was consumed, with selectivity to desired epoxide of 68%.

EXAMPLE 42

Epoxidation of cyclooctadiene

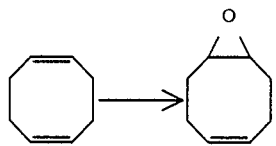

Cyclooctadiene was epoxidized by the above procedure, using Di(acetate)₃ as catalyst (1% based on the weight of starting material) and acetone as solvent (volume ratio solvent to starting material 3:1). The final mol ratio propionaldehyde to starting material was 1.6:1, oxygen was bubbled through at a rate of 8 liters/hour, and reaction time was 5 hours.

91% conversion of starting material was obtained, with selectivity to desired mono epoxide product by 78%. Small amounts of diols, esters and diepoxide were present in the product.

By comparison, when Mn(acetate)₃/Co(acetate)₂ (100:1 by weight) was used as catalyst in a comparable procedure, with ethyl acetate as solvent, after 8 hours reaction time 61% of starting material was consumed, with selectivity to desired epoxide of only 52%. Ketones, esters and diols were produced, with formation of a black precipitate.

EXAMPLE 43

Epoxidation of 1,5-dimethylcyclooctadiene

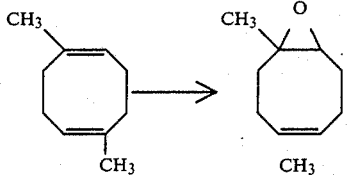

1,5-dimethylcyclooctadiene was epoxidized by the above-described procedure, using Di(acetate)₃./Co(acetate)₂ (100:1 by weight) as catalyst (0.8% based on the weight of starting material) and ethyl acetate as solvent (volume ratio solvent to starting material 2.5:1). The final mol ratio propionaldehyde to starting material was 1.5:1, air was bubbled through at a rate of 14 liters/hour, and reaction time was 4 hours.

More than 96% conversion of starting material was obtained, with selectivity to desired epoxide product of 76%.

By comparison, when Mn(acetate)₃ was used as catalyst in a comparable procedure, with ethyl acetate as solvent, after 6.5 hours reaction time 92% of starting material was consumed, with selectivity to desired epoxide of less than 10%.

EXAMPLE 44

Epoxidation of 1,4-dimethyl[3.3.0]bicyclooct-3-ene

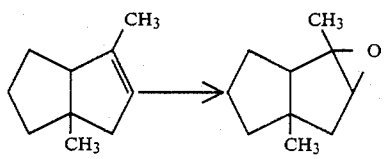

1,4-dimethyl[3.3.0]bicyclooct-3-ene was epoxidized by the above-described procedure, using Di(acetate)₃./Co(acetate)₂ (100:1 by weight as catalyst (0.6% based on the weight of starting material) and ethyl acetate as solvent (volume ratio solvent to starting material 3:1). The final mol ratio propionaldehyde to starting material was 1.5:1, oxygen was bubbled through at a rate of 6 liters/hour, and reaction time was 3 hours.

More than 96% conversion of starting was obtained, with selectivity to desired epoxide product of 91%.

EXAMPLE 45

Epoxidation of naturally-occurring caryophyllene

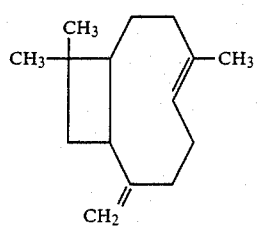

(caryophyllene + isocaryophyllene) 91%

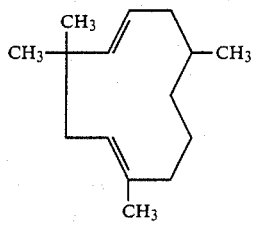

(α-carophyllene) (2 isomers) 8%

Naturally-occurring caryophyllene was epoxidized by the above-described procedure, using Di(acetate)₃ as catalyst (1% based on the weight of starting material) and acetone as solvent (volume ratio solvent to starting material 2:1). The final mol ratio propionaldehyde to starting material was 2:1, oxygen was bubbled through at a rate of 10 liters/hour, and reaction time was 8 hours.

91% conversion of starting material was obtained, with selectivity to desired epoxide product of 84%.

This reaction was repeated using Di(acetate)₃./Co(acetate)₂ (100:1 by weight) as catalyst (1% based on the weight of starting material) and ethyl acetate as solvent (volume ratio solvent to starting material 3:1). The final mol ratio propionaldehyde to starting material was 2:1, oxygen was bubbled through at a rate of 10 liters/hour, and reaction time was 6 hours.

92% conversion of starting material was obtained, with selectivity to mono epoxide product of 81%.

By comparison, when Mn(acetate)₃/Co(acetate)₂ (100:1 by weight) was used as catalyst in a comparable procedure, with acetic acid as solvent, after 4.5 hours reaction time 94% of starting material was consumed, with selectivity to mono epoxide of only 52%.

EXAMPLE 46

Epoxidation of cedar-wood terpenes

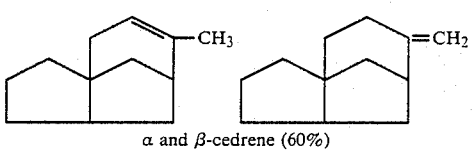

α and β-cedrene (60%)

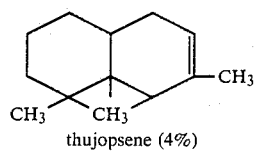

thujopsene (4%)

Naturally-occurring cedar-wood terpenes (cedrene) were epoxidized by the above-described procedure, using Di(acetate)$_3$ as catalyst (1% based on the weight of starting material) and acetone as solvent (volume ratio solvent to starting material 3:1). The final mol ratio propionaldehyde to starting material was 2:1, oxygen was bubbled through at a rate of 6 liters/hour, and reaction time was 8 hours.

88% conversion of starting material was obtained, with selectivity to desired epoxide product of 68%.

By comparison, when Mn(acetate)$_3$/Co(acetate)$_2$ (100:1 by weight) was used as catalyst in a comparable procedure, with acetic acid as solvent, after 5 hours reaction time 96% of starting material was consumed, with selectivity to desired epoxide of only 5%, most of the product being a mixture of ketones and acids.

EXAMPLE 47

Epoxidation of α and β-chamigrene

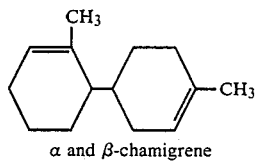

α and β-chamigrene

α and β-chamigrene were epoxidized by the above-described procedure, using Di(acetate)$_3$/Co(acetate)$_2$ (100:1 by weight) as catalyst (1% based on the weight of starting material) and ethyl acetate as solvent (volume ratio solvent to starting material 2:1). The final mol ratio propionaldehyde to starting material was 1.5:1, oxygen was bubbled through at a rate of 10 liters/hour, and reaction time was 9 hours.

92% conversion of starting material was obtained, with selectivity to mono epoxide product of 78%.

EXAMPLE 48

Epoxidation of 4-terpeneol

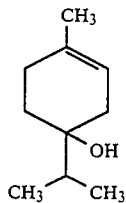

4-terpeneol was epoxidized by the above-described procedure, using Di(propionate)$_3$/Co(propionate)$_2$ (100:1 by weight) 20% solution in propionic acid) as catalyst (0.6% based on the weight of starting material) and acetone as solvent (volume ratio solvent to starting material 1.5:1). The final mol ratio propionaldehyde to starting material was 1.5:1, oxygen was bubbled through at a rate of 6 liters/hour, and reaction time was 4.5 hours.

More than 96% conversion of starting material was obtained, with selectivity to desired epoxide product of 87%.

EXAMPLE 49

Epoxidation of 8-terpenol

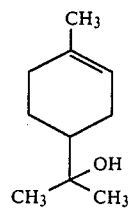

8-terpenol was epoxidized by the above-described procedure, using Di(propionate)$_3$/UO$_2$(propionate)$_2$/Co(propionate)$_2$ (1:0.72:10$^{-5}$ by weight) (10% in propionic acid) as catalyst (0.5% based on the weight of starting material) and acetone as solvent (volume ratio solvent to starting material 2.5:1). The final mol ratio propionaldehyde to starting material was 1.1:1, oxygen was bubbled through at a rate of 6 liters/hour, and reaction time was 7 hours.

52% conversion of starting material was obtained, with selectivity to desired epoxide product of 81%.

COMPARATIVE EXAMPLES O TO Q

When isophorone was subject to comparable procedures using Di(acetate)$_3$/Co(acetate)$_2$ (100:1 by weight) (1% based on weight of starting material), ethyl acetate as solvent (volume ratio solvent to starting material 3:1), final mol ratio propionaldehyde to starting material of 1.:1, and bubbling oxygen through a rate of 12 liters/hour for a reaction time of 16 hours, less than 5% of starting material was consumed and no epoxide was produced.

Similarly, attempts to epoxidize terpinolene and γ-terpinene failed to yield epoxide products.

As the terminology is used in this specification, didymium describes a mixture comprising various elements of the lanthanum series including praseodymium, which may be either a naturally-occuring mixture or a mixture which has been processed to remove and/or concentrate one or more of its metals.

What is claimed is:

1. A process for epoxidizing an olefinic double bond in an olefinically-unsaturated compound other than an α,β-unsaturated carboxylic acid or a compound having a six-membered ring of carbon atoms wherein 3 or 4 of the ring atoms have sp$^2$ hybrid orbitals, which comprises contacting a liquid phase mixture containing the olefinically-unsaturated compound, an aldehyde having at least two carbon atoms in a quantity of at least about one mol of said aldehyde per mol of olefinically-unsaturated compound, and a solvent with molecular oxygen in the presence of a catalyst which comprises a praseodymium compound in solution in the said liquid phase.

2. The process according to claim 1, wherein the aldehyde has between two and four carbon atoms, inclusive.

3. The process according to claim 2, wherein the sovlent comprises at least one compound selected from C$_1$ to C$_6$ alkyl esters of C$_2$ to C$_6$ ketones, C$_3$ to C$_6$ ketones and C$_2$ to C$_6$ carboxylic acids.

4. A process according to claim 3, wherein the catalyst comprises a C$_2$ to C$_6$ carboxylic acid salt of praseodymium.

5. The process according to claim 4, wherein the catalyst also comprises a cobalt compound.

6. The process according to claim 4, wherein the catalyst also comprises a uranium or vanadium salt.

7. The process according to claim 4, wherein the carboxylic acid salt is an acetate or propionate salt.

8. The process according to claim 7, wherein the catalyst also comprises a cobalt or uranium or vanadium compound.

9. The process according to claim 4, wherein the aldehyde is present in the liquid phase mixture in a quantity in the range from about 1 to 3 mols per mol of olefinically-unsaturated compound and the temperature of the liquid phase mixture is in the range from about 30° C. to the reflux temperature of the reaction mixture.

10. The process according to claim 9, wherein the temperature is in the range from about 30° C. to 60° C.

11. The process according to claim 1, wherein the olefinically-unsaturated compound is a $C_3$ to $C_{30}$ olefin having from 1 to about 6 olefinic double bonds.

12. The process according to claim 11, wherein the olefinically-unsaturated compound contains in the molecule one or more substitutents selected from the group consisting of ketonic carboxyl groups, alicyclic rings of 3 to 12 ring atoms, —OH groups, —COOH groups, —CHO groups, —OR groups, —COOR groups, and —OCOR groups, wherein R represents an alkyl or aryl group.

13. The process of claim 11, wherein the aldehyde is an aliphatic aldehyde having between 2 and 4 carbon atoms inclusive, and the solvent comprises at least one compound selected from $C_1$ to $C_6$ alkyl esters of $C_2$ to $C_6$ carboxylic acids, $C_3$ to $C_6$ ketones, and $C_2$ to $C_6$ carboxylic acids.

14. The process of claim 13, wherein the catalyst comprises one or more organic salts of praseodymium.

15. The process according to claim 14, wherein the organic salts are one or more $C_2$ to $C_6$ carboxylic acid salts.

16. The process according to claim 15, wherein the organic salts are one or more salts selected from the group consisting of acetate and propionate salts.

17. The process of claim 16, wherein the catalyst comprises a didymium salt.

18. The process of claim 11, wherein the catalyst comprises one or more organic salts or praseodymium.

19. The process of claim 18, wherein the catalyst comprises one or more $C_2$ to $C_6$ carboxylic acid salts of praseodymium.

20. The process of claim 12, wherein the catlayst comprises one or more organic salts of praseodymium.

21. The process of claim 20, wherein the catalsyt comprises one or more $C_2$ to $C_6$ carboxylic acid salts of praseodymium.

22. The process of claim 11, wherein the catalyst comprises one or more organic salts of praseodymium.

23. The process of claim 1, wherein the catalyst comprises one or more $C_2$ to $C_6$ carboxylic acid salts of praseodymium.

24. The process of claim 23, wherein the catalyst comprises one or more salts selected from the group consisting of acetate and propionate salts of praseodymium.

25. The process of claim 24, wherein the catalyst additionally comprises one or more salts of one or more metals selected from the group consisting of cobalt, uranium, and vanadium.

26. The process of claim 25, wherein the catalyst comprises a didymium salt.

27. The process of claim 22, wherein the catalyst comprises a didymium salt.

* * * * *